(54) IONTOPHORESIS, ELECTROPORATION AND COMBINATION CATHETERS FOR LOCAL DRUG DELIVERY TO ARTERIES AND OTHER BODY TISSUES (75) Inventors: Charles L. Brown, III, Atlanta, GA (US); Neville Crawford, Wetherby; Steven Freear, Leeds, both of (GB)

(73) Assignee: Global Vascular Concepts, Inc., Atlanta, GA (US)

( * ) Notice: Subject to any disclaimer, the term of this patent is extended or adjusted under 35 U.S.C. 154(b) by 0 days.

(21) Appl. No.: 09/253,272

(22) Filed: Feb. 19, 1999

Related U.S. Application Data (60) Provisional application No. 60/081,682, filed on Apr. 14, 1998.

(51) Int. Cl.[7] .................................................. A61N 1/30

(52) U.S. Cl. ............................................. 604/20; 604/501

(58) Field of Search ................................. 604/96, 101, 20, 604/21, 22, 501; 606/113, 198, 127

(56) References Cited

U.S. PATENT DOCUMENTS

| | | |
|---|---|---|
| 5,232,441 | 8/1993 | Stephen et al. . |
| 5,236,413 | 8/1993 | Feiring . |
| 5,256,141 | 10/1993 | Gencheff et al. . |
| 5,282,785 | 2/1994 | Shapland et al. . |
| 5,286,254 | 2/1994 | Shapland et al. . |
| 5,304,120 * | 4/1994 | Crandell et al. ........................ 604/96 |
| 5,318,514 | 6/1994 | Hofmann . |
| 5,401,239 | 3/1995 | Stephen et al. . |
| 5,419,763 | 5/1995 | Hildebrand . |
| 5,423,744 | 6/1995 | Gencheff et al. . |
| 5,425,703 | 6/1995 | Feiring . |
| 5,458,568 | 10/1995 | Racchini et al. . |
| 5,462,520 | 10/1995 | Hofmann . |
| 5,464,386 | 11/1995 | Hofmann . |
| 5,498,238 | 3/1996 | Shapland et al. . |
| 5,499,971 | 3/1996 | Shapland et al. . |
| 5,501,662 | 3/1996 | Hofmann . |
| 5,505,700 | 4/1996 | Leone et al. . |
| 5,507,724 | 4/1996 | Hofmann et al. . |
| 5,549,603 | 8/1996 | Feiring . |
| 5,554,119 | 9/1996 | Harrison et al. . |
| 5,569,198 | 10/1996 | Racchini . |
| 5,588,961 | 12/1996 | Leone et al. . |
| 5,612,207 | 3/1997 | Nicolau et al. . |
| 5,628,730 | 5/1997 | Shapland et al. . |
| 5,634,899 | 6/1997 | Shapland et al. . |
| 5,636,634 | 6/1997 | Kordis et al. . |
| 5,669,874 | 9/1997 | Feiring . |
| 5,688,233 | 11/1997 | Hofmann et al. . |
| 5,704,908 | 1/1998 | Hofmann et al. . |
| 5,720,921 | 2/1998 | Meserol . |
| 5,728,068 | 3/1998 | Leone et al. . |
| 5,730,698 * | 3/1998 | Fischell et al. . |
| 5,749,845 | 5/1998 | Hidebrand et al. . |
| 5,779,661 | 7/1998 | Stephen et al. . |
| 5,800,392 | 9/1998 | Racchini . |
| 5,807,306 * | 9/1998 | Shapland et al. ........................ 604/21 |
| 5,810,763 | 9/1998 | Feiring . |

(List continued on next page.)

Primary Examiner—Anhtuan T. Nguyen
Assistant Examiner—Michael M Thompson
(74) Attorney, Agent, or Firm—Sutherland Asbill & Brennan LLP (57) ABSTRACT

Catheter-based devices for enhancing the local delivery of drugs, pharmaceuticals, plasmids, genes, and other agents into the wall tissues of tubular compartments of the living body. One catheter device provides an electrical driving force that can increase the rate of migration of drugs and other therapeutic agents out of a polymer matrix into body tissues and cells using iontophoresis only. Another device uses iontophoresis only, electroporation only, or combined iontophoresis and electroporation. In the latter device, the two procedures may be applied sequentially in any order without removing or repositioning the catheter.

20 Claims, 4 Drawing Sheets

U.S. PATENT DOCUMENTS

| | | |
|---|---|---|
| 5,843,016 | 12/1998 | Lugnani et al. . |
| 5,852,058 | 12/1998 | Cooke et al. . |
| 5,865,787 | 2/1999 | Shapland et al. . |
| 5,897,334 | 4/1999 | Ha et al. . |
| 5,944,710 | 8/1999 | Dev et al. . |
| 5,968,006 | 10/1999 | Hofmann . |
| 5,993,434 | 11/1999 | Dev et al. . |

\* cited by examiner

Fig_6

IONTOPHORESIS, ELECTROPORATION AND COMBINATION CATHETERS FOR LOCAL DRUG DELIVERY TO ARTERIES AND OTHER BODY TISSUES

This application claims benefit of provisional applications 60/081682, filed Apr. 14, 1998.

FIELD OF THE INVENTION

The present invention relates in general to devices for enhancing the local delivery of drugs, pharmaceuticals, plasmids, genes, and other agents into tissues or cells of the living body. In particular, the present invention relates to catheter-based devices which provide an electrical driving force that can increase the rate of migration of drugs and other therapeutic agents out of a polymer matrix into body tissues and into cells using iontophoresis only, electroporation only, or combined iontophoresis and electroporation. The two procedures may be applied sequentially in any order without removing or repositioning the catheter. In addition, the present invention relates to catheter devices which, if used in arteries, veins, or compartments of the heart to electrically enhance drug delivery to the tissues, do not seriously compromise blood flow through the vessel during treatment.

BACKGROUND OF THE INVENTION

Treatment agents, such as medicines, are generally administered to the body by various methods, such as topical application, oral ingestion, intravascular, intramuscular or parenteral injection and, less commonly, by aerosol insufflation and by transdermal iontophoresis. In all of these treatments there is an immediate dilution effect greatly reducing the concentration of the agent to which the target tissues or cells are exposed. Also, medicines administered by these systems may be more vulnerable to processes such as metabolic degradation, inactivation by binding to plasma proteins or accelerated clearance from the body. These processes adversely affect the drug's concentration and residence time in the target tissues and reduce its therapeutic efficacy.

Most of the above modes of drug administration also expose non-target tissues, i.e. those that do not require treatment, to the action of the drugs, with the consequent risk of serious side effects. It is this risk towards non-target tissues that reduces a drug's efficacy by restricting systemic concentrations to a threshold level above which side effects would become unacceptable.

Local drug delivery procedures can obviate some of the metabolic breakdown, early clearance and side effect problems affecting efficacy by presenting therapeutic concentrations of a drug only to the target site, minimizing effects upon non-target tissues. The reduction in quantity of a drug required minimizes side effects and can also result in lower treatment costs.

Recognition of the advantages of local delivery strategies has stimulated the development of a number of catheter-based delivery devices which apply drugs directly to the body tissues at specific locations, often to sites that would be otherwise inaccessible without surgery. However, if the specific target for an agent is intracellular, simple local application of the drug, followed by its passive diffusion into tissues, does not facilitate movement of the drug across cell surface membrane barriers into intracellular compartments. Diffusion away from the target cells occurs and high extracellular concentrations are rarely sustained long enough to mediate significant passage into the cells. Some drugs penetrate intact cell membranes by diffusion only very poorly and may require specific carrier or bulk transport by a phagocytic or pinocytic mechanism, to penetrate the cell membrane. These natural transport systems operate inefficiently, or not at all, when the tissues are affected by disease.

Double balloon catheters have been used to confine a drug solution to a specific segment of a blood vessel requiring treatment. For this use, internal lumens in the catheter are needed to transport the liquid drug to the isolated compartment and to evacuate any remaining drug after treatment. Apart from the dangers in occluding blood flow with the balloons and the associated ischaemic risk, any downstream leakage due to defective balloon sealing can also result in overdosing of the drug. Moreover, much drug can be lost through side branches arising from the vessel in the isolated segment between the balloons.

Devices have also been developed to try to improve the depth of penetration into tissue by pressure driving a solution of the drug into the vessel wall via tiny orifices in the fabric of a balloon. There is, however, some evidence that high pressure "jetting" of a drug solution out of small pores close to the vessel lumen can in fact cause vessel wall injury. The development of double skinned, microporous (or weeping) balloons obviated this "jetting" effect to some extent, but diffusion of the drug into the vessel wall is still slow, and much of the drug can be lost through subsequent "washout effects".

Iontophoretic catheters have been used in some animal angioplasty studies to provide an electrical driving force for movement of a drug into tissues. This technique requires that the agent to be delivered carries an electrical charge under the local physiological pH conditions. While iontophoresis does enhance the delivery of drugs into body tissues, it has been shown in transdermal iontophoresis ("TDI"), that migration of drugs through skin predominantly occurs via extracellular pathways (sweat glands and hair follicle channels) where the current densities are much higher than elsewhere. This preferential channel movement can be favorable towards providing high drug concentrations in the skin capillary bed and onward into the circulation. However, with other tissues, such as blood vessels, the delivery of drugs to the vessel wall cells will be of low efficiency.

Angioplasty procedures generally involve the introduction of a small balloon catheter into the femoral artery in a patient's leg and, with the help of a guide wire, the catheter is passed by remote manipulation under fluoroscopy into the heart. The balloon can then be positioned in a region of a coronary artery that has become constricted due to atherosclerosis and by inflating and deflating the balloon several times the bore of the diseased artery is mechanically widened until a satisfactory blood flow through the vessel has been restored. If the artery is severely damaged by disease, and perhaps hardened by calcium deposition, this balloon inflation may also cause some degree of additional injury with local de-endothelialisation and exposure of underlying extracellular matrix components such as collagen and elastin. In a few patients excessive recruitment of platelets and fibrinogen can then result in an acute thrombotic occlusion. This is now less common, however, with the routine use of heparin and aspirin cover during the angioplasty procedure.

Generally, angioplasty procedures produce excellent results obviating the need for bypass surgery, but in about 30–40% of patients, an ostensibly successful initial dilatation of the artery may be followed by a renarrowing of the vessel (restenosis) some 3 to 9 months later. If this restenosis is severe, these patients may require a second angioplasty procedure, often with implantation of a stent to act as a scaffold in the vessel. In other cases arterial reconstruction under by-pass surgery, which is a higher risk procedure, may be required. With more than 800,000 PTCA procedures now performed world-wide annually, the socio-economic implication of this 30–40% restenosis rate has become a matter of serious concern to interventional cardiologists.

The pathophysiology of this late restenosis is complex, and involves a wide range of cellular and molecular responses, many of which are not yet fully understood. Although a number of putative targets for drug interference have been identified, more than 50 clinical trials (some large and multi-center) with a wide range of different drugs have failed to reveal a satisfactory pharmacotherapeutic approach to reducing the incidence of restenosis. One problem is that for some of the potentially useful drugs, it is not possible by systemic administration to get a therapeutically effective level of the drug in the vessel wall tissue without significantly affecting non-target tissues elsewhere.

Accordingly, what is needed are devices for delivering treatment agents to specific locations, including intracellular locations in a safe and effective manner. These devices would deliver the agents to a diseased site in effective amounts without endangering normal tissues or cells and thus reduce or prevent the occurrence of undesirable side effects.

SUMMARY OF THE INVENTION

The present invention is directed to devices for electrically enhancing the local delivery of treatment agents into the wall tissues or cells of the living body. These devices are designed to target certain tissue and cell locations and deliver the treatment agents directly to those locations, while minimizing any effects on non-targeted tissues and cells.

In particular, the present invention relates to catheter-based devices which provide an electrical driving force that can increase the rate of migration of drugs and other therapeutic agents out of a polymer matrix into body tissues and cells using iontophoresis only, electroporation only, or combined iontophoresis and electroporation. A preferable approach may be for electroporation to be applied to permeabilize the cells after pre-iontophoresis of the agent into the tissues. Preferably, the catheter is able to perform the two procedures sequentially without repositioning of the catheter. Even more preferably, the catheter is designed to maintain a high concentration of drug in the tissue extracellular spaces (e.g. by iontophoresis) such that the subsequent creation of transient pores in cell surface membranes by electroporation pulses results in greatly improved intracellular delivery of the treatment agent. In addition to applying electrical driving forces to enhance local delivery of chemotherapeutic agents to blood vessel walls and to tumor sites where the targets are intracellular, the present inventions can also be used for treatment of microbial and viral infections. Here the efficacy of an otherwise potent drug can be hampered by it's inability to reach intracellular compartments harboring the microorganisms.

The present invention is particularly applicable to the local delivery of drugs during interventional cardiology procedures such as angioplasty, stent implantation etc. Unlike balloon based electrical drug delivery catheters, where electrodes are mounted on the surface of a porous balloon or on the catheter itself within the balloon, the electrodes in the present inventions are part of an expandable open mesh network. When this network expands to press against the vessel wall, interstices open allowing blood to continue to flow through the vessel during electrical pulsing and drug delivery. With this novel feature, extended treatment times are possible since the risk of ischaemia in adjacent tissue is reduced.

The present devices are also capable of generating high local field strengths using a low voltage input. Additionally, since the catheter devices are similar in operation to current angioplasty catheter devices, operators will have an initial familiarity with operating the devices of the present invention. For example the present devices can be used in conjunction with conventional introducers, guide wires, guiding catheters and sleeves etc, and the electrode array has intrinsic radio opacity which assists localization to the tissue treatment site.

Accordingly, it is an object of the present invention to provide devices for electrically enhancing the local delivery of drugs, pharmaceuticals, plasmids, genes, and other agents.

It is another object of the present invention to provide devices for the local delivery of treatment agents into the wall tissues or cells of the living body.

It is another object of the present invention to provide devices which use iontophoresis and/or electroporation to enhance the local delivery of treatment agents.

It is another object of the present invention to provide devices which are able to deliver treatment agents to specific tissues and cells without endangering non-targeted tissues and cells.

It is another object of the present invention to provide devices which can be used in blood vessels to electrically enhance drug delivery to the vessel wall without severely compromising blood flow within the vessel. Longer treatment times are then possible without the risk of ischaemia of nearby tissues.

These and other objects, features and advantages of the present invention will become apparent after a review of the following detailed description of the disclosed embodiments and the appended claims.

DETAILED DESCRIPTION

The present invention is directed to devices for electrically enhancing the local delivery of treatment agents, such as drugs, pharmaceuticals, plasmids, genes, and other agents, into the wall tissues or cells of the living body. These devices are constructed and arranged to target certain tissue and cell locations and deliver the treatment agents directly to those locations, while minimizing any effects of the treatment agents on non-targeted tissues and cells.

In particular, the present invention relates to catheter-based devices which provide an electrical driving force that can increase the rate of migration of drugs and other therapeutic agents out of a polymer matrix into body tissues and cells using iontophoresis only, electroporation only, or combined iontophoresis and electroporation. For delivering iontophoresis pulses, all of the SS electrode wires in the first embodiment catheter or all the paired copper electrodes in the second embodiment PCB catheter are switched at the power supply to the same electrical polarity. The polarity is chosen according to the charge characteristic of the drug molecule to be delivered. A second "plate" electrode of opposite polarity is placed on the patient's skin or other body region to provide the potential or current flow required to iontophorese the drug or agent into the target tissue. Alternatively, the tip of the guide wire emerging from the distal end of the catheter may be used as the second electrode.

For electroporation of the tissue using the second embodiment, the electrodes of each pair on the PCB strips are separately energized to opposite polarities so that a field is generated across the electrode gaps.

In certain situations, a preferable approach is for electroporation to be applied to permeabilize the cells after pre-iontophoresis of the treatment agent into the tissues. Preferably, the catheter is able to perform the two procedures sequentially without repositioning of the catheter. Even more preferably, the catheter is designed to maintain a high concentration of drug in the tissue extracellular spaces (e.g. by iontophoresis) such that the subsequent creation of transient pores in cell surface membranes by electroporation pulses results in greatly improved intracellular penetration of the treatment agent.

The design of the catheters of the present invention may vary depending on the treatment agent to be delivered and the place into which the agent is to be delivered. However, since procedural simplicity and device familiarity are important considerations, the catheters preferably resemble, in profile, a conventional over the wire balloon angioplasty catheter, but without the balloon. These catheters would be capable of passing smoothly through a conventional introducer, which would usually be shaped at the distal end according to the target vessel anatomy. During insertion into the patient, the catheter can be housed in a sheath to protect the drug depot (i.e. the region of hydrogel coating) until the treatment site is reached. When correctly positioned, the catheter can be pushed out of the protective sheath and the electrode array expanded for close juxtaposition to the tissue treatment zone. Similarly for ease of withdrawal of the catheter device from the body the relaxed electrode network can be rehoused in the sheath.

Alternative embodiments for the electrodes are described briefly. In a first embodiment, which is for iontophoresis only, the electrodes preferably comprise stainless steel wire, having polyester monofilament strands intercalated between to form an expandable tubular braid held by ferrules around a segment of a support catheter.

In a second embodiment, the electrode array is preferably a slotted polyimide/copper printed circuit board (PCB) sheet which is formed into a cylinder around a catheter body and held by ferrules at each end. The parallel slots produce a series of PCB strips which expand into a "Chinese lantern" configuration when the ferrules are moved towards each other. The outer surface of each strip then has paired electrodes of opposite polarities etched into the copper coating. A thin layer of gold preferably covers the whole PCB surface to prevent oxidation.

Preferably, the catheter has an internal lumen in the support catheter to take a guide wire for the maneuverability, torque control and other desirable properties for the catheter. Additionally, there may be one or more smaller internal lumens for wire leads to pass through the catheter body to energize electrodes mounted on the catheter near the distal tip. These wire leads may be energized from a power supply unit sited outside the body. In both embodiments, the lumen leads connect to the electrodes within the distal fixed ferrule.

The present invention allows for the electrical enhancement of drug delivery within any bodily compartment or cavity, for example, a coronary, renal or carotid artery. The drug delivery may be carried out during an angioplasty procedure or perhaps preparatory to or during implantation of a stent. The present catheters set forth may also be substituted for a balloon catheter after the sequence of balloon dilatation has been completed and the balloon withdrawn or after deployment of a stent. However, whereas a stent of conductive material may well enhance drug delivery when the catheters are used in the iontophoresis mode, such a stent may interfere with the field diagram of the paired electrodes when used in the electroporation mode. In this event, electrically enhanced drug delivery should be carried out before stent deployment.

In some circumstances it may be appropriate to institute a drug delivery therapy (for example with an agent which softens atherosclerotic plaques) before balloon dilatation or before stent implantation is performed. In this situation, the present catheter would be withdrawn and the angioplasty catheter or the balloon mounted stent would be passed into the artery through the same introducer.

For some treatment protocols, simple iontophoretic enhancement of local drug delivery may suffice. However, for others, such as cancer chemotherapy, electroporation only of the cells in a particular region of tissue would be used to facilitate the intracellular penetration of a cytotoxic agent, such as bleomycin or cisplatin, present in the systemic circulation. In such application, no hydrogel drug depot is required on the electroporation electrodes. Providing high doses of a drug within target cells in this way may avoid the need for sustaining systemic concentrations of levels where side effects become a serious problem.

For localized drug delivery to tissues in vivo, the combined use of both iontophoresis and electroporation procedures in sequence may be performed. For such a sequential process, a drug would be delivered from the catheter into the tissue by pre-iontophoresis to give a high concentration of the treatment agent in the extracellular space. The iontophoresis pulsing would be followed immediately by electroporation pulsing to permeabilize the membranes of cells within the tissue. A rapid gradient-driven diffusion of the treatment agent into the transiently permeabilized cells would facilitate targeting of the agent to intracellular elements and metabolic pathways at a concentration that is therapeutically effective. One of the catheter embodiments discussed herein is capable of performing these sequential processes without repositioning of the catheter by simple switching at the power supply outside the body. In a further variation in this catheter design, separate collector plates for the different PCB strips can be designed into the PCB circuitry. These can be connected to separate wires in the ferrule extending through lumens in the catheter body to the power supply unit. By simple switching, the electrode pairs in the PCB strips can be selectively energized in either the iontophoresis or electroporation mode. This facility allows for an even more localized treatment of a region of tissue (for example, in an artery) where a lesion site is eccentrically located in the lumen, without applying electrical energy to nearby normal or non-target tissue.

As used herein, the term "iontophoresis" means the migration of ionizable molecules through a medium driven by an applied low level electrical potential. This electrically mediated movement of molecules into tissues is superimposed upon concentration gradient dependent diffusion processes. If the medium or tissue through which the molecules travel also carries a charge, some electro-osmotic flow occurs. However, generally, the rate of migration of molecules with a net negative charge towards the positive electrode and vice versa is determined by the net charge on the moving molecules and the applied electrical potential. The driving force may also be considered as electrostatic repulsion. Iontophoresis usually requires relatively low constant DC current in the range of from about 2–5 mA. In a well established application of iontophoresis, that of enhancing drug delivery through the skin (transdermal iontophoresis), one electrode is positioned over the treatment area and the second electrode is located at a remote site, usually somewhere else on the skin. With the present invention the return electrode may be similarly positioned on the skin. Alternatively the tip of the guide wire emerging from the distal end of the support catheter may serve as the return electrode. The applied potential for iontophoresis will depend upon number of factors, such as the electrode configuration and position on the tissue, the nature and charge characteristics of the molecules to be delivered, and the presence of other ionic species within the polymer matrix and in the tissue extracellular compartments.

As used herein, the term "electroporation" means the temporary creation of holes or aqueous pores in the surface of a cell membrane by an applied electrical potential and through which therapeutic agents may pass into the cell. Electroporation is now widely used in biology, particularly for transfection studies, where plasmids, DNA fragments and other genetic material are introduced into living cells. During electroporation pulsing, molecules which are not normally membrane permeant are able to pass from the extracellular environment into the cells during the period of induced reversible membrane permeabilization. The permeabilized state is caused by the generation of an electrical field in the cell suspension or tissue of sufficient field strength to perturb the cell surface membrane's proteolipid structure. This perturbation (sometimes referred to as dielectric breakdown) is believed to be due to both a constituent charge separation and the effect of viscoelastic compression forces within the membrane and it's sub-adjacent cytoskeletal structures. The result is a localized membrane thinning. At a critical external field strength, pores or small domains of increased permeability are formed in the membrane proteolipid bi-layer.

During this short period of permeabilization, external agents can rapidly transfer across the surface membrane via these pores and become encapsulated within the cell's cytosol compartment when the membrane reseals. With appropriate electrical parameters for the poration (field strength, pulse width, number of pulses etc), resealing of the membrane begins almost immediately after the pulsing, and little, if any, leakage of cytosol constituents occurs. Providing that a threshold field strength has not been exceeded, the surface membrane can reorganize with a full restoration of it's former structural integrity, receptor status and other functional properties. The resealing rate is temperature sensitive (with an optimum temperature around 37° C.). The temperature depends on the phase transition temperature of lipids in the membrane bi-layer and the capacity of proteins, and other integral membrane constituents, to diffuse laterally within the bi-layer. Too high a field strength can cause membrane breakdown beyond it's capacity to reseal the electropores.

Electrical fields for poration are commonly generated by capacitor discharge power units using pulses of very short (micro to millisecond) time course. Square wave and radio frequency pulses have also been used for cell electroporation. Of the commercially available power supplies suitable for electroporation, the ECM Voltage Generator ECM 600, available from BTX Inc of San Diego Calif., generates an exponential decay pulse which can be adjusted through resistor selection and different capacitor ranges to give pulse lengths in the range microseconds to milliseconds suitable for electroporating living cells. With narrow electrode gap widths such as the 0.1 or 0.2 mm gaps suggested here for the PCB electrode pairs, appropriate field strengths for tissue electroporation are possible (Kvolts/cm) using low, physiologically acceptable input voltages.

To date, most of the literature reports on electroporation have been concerned with cells in suspension and there is little if any background on cells resident in tissues. It has been reported that cells in monolayer culture, simulating an attached epithelium, require lower field strengths for successful poration (as indexed by higher transfection rates) than the same cells in free suspension. Moreover, cells in tissues which are in electrical contact or which can communicate by molecular conversation with neighbor cells through junctions can generally be electroporated at lower field strengths than the same cells in which are in a single cell suspension.

Animal cells in suspension can be electroporated with field strengths in the range 0.5 to 7.0 Kvolts/cm and the critical field strength for successful permeabilisation with resealing varies inversely with cell size, at least for cells which are approximately spherical in shape. It is this inverse relationship that allows the application of a field strength sufficient to porate a cell's surface membrane without disruption of the boundary membranes of important intracellular organelles and other structures.

Although the present inventions may have wider application in locally delivering drugs to many different tubular tissues of the body, particular applications preferred are in percutaneous transluminal coronary angioplasty ("PTCA"), after stent implantation and during arterial and venous graft implantation.

PTCA is regarded as a preferred lower risk alternative to bypass surgery when one or more arteries of the heart have become constricted due to disease. Inadequate arterial blood flow compromises the oxygenation of nearby heart tissue and if untreated, irreversible myocardial dysfunction and necrosis can result.

Two preferred catheter embodiments are set forth below. The first embodiment is preferably used only for iontophoretically enhanced drug delivery. The second embodiment may be used for enhancing the local delivery of drugs by either iontophoresis only, electroporation only or both procedures applied sequentially.

Figure 1:
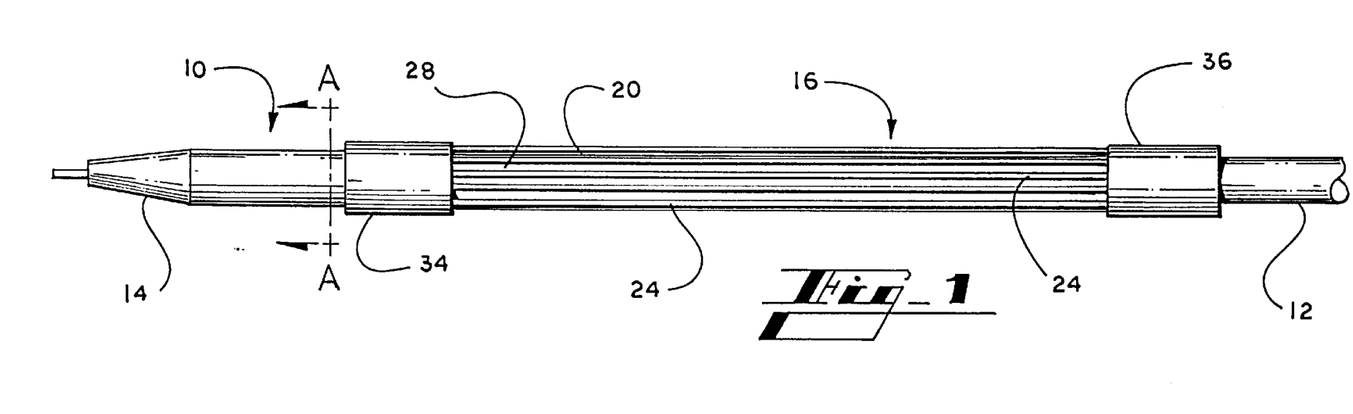
FIG. 1 shows a catheter-based device for drug delivery according to its relaxed position.

As shown in FIG. 1, the catheter 10 has a proximal end 12 and a distal end 14. At the proximal end 12 of the support catheter 10, in a position normally occupied by a balloon, is a short (~4–6 cm) expandable tubular braided sleeve 20, comprising wires or electrodes 24 mounted around and parallel to the catheter body 16. The sleeve 20 may also comprise polyester monofilaments 28 (preferably of the same thickness as the wire electrodes) intercalated between the electrodes 24 during the braiding process. Alternatively, while the electrodes 24 may be made from a metal, such as copper, gold, platinum, stainless steel, or silver, the electrodes may also be made of carbon fiber filaments.

Figure 2:
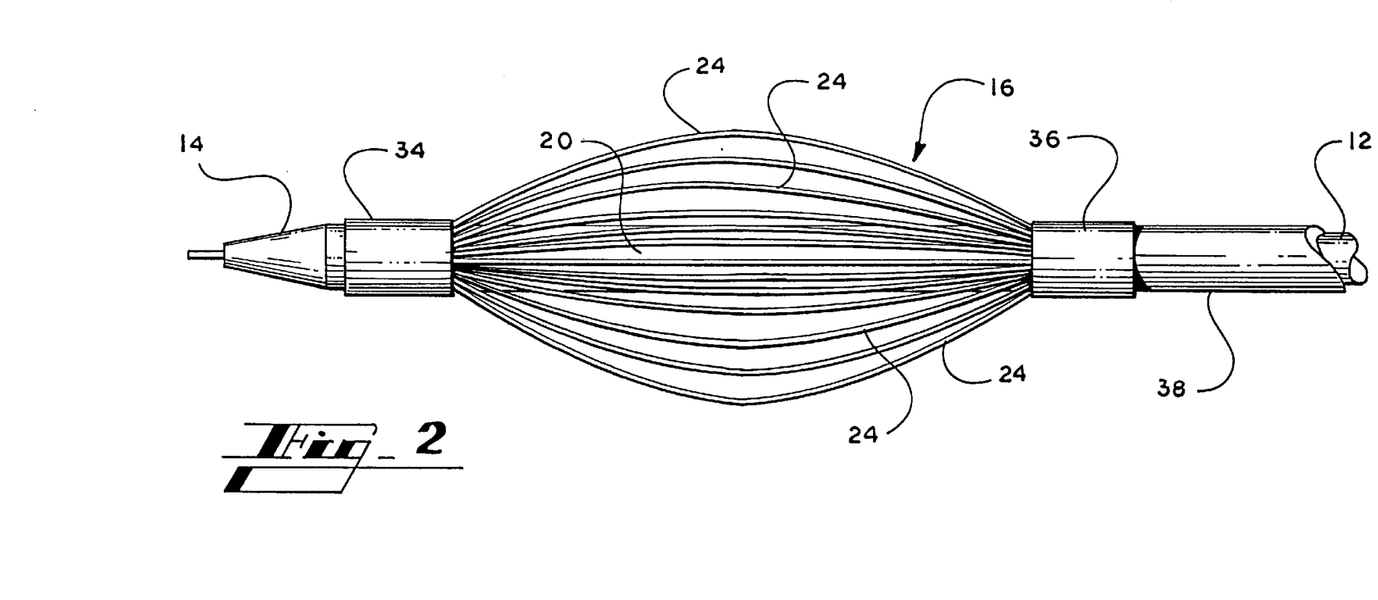
FIG. 2 shows a catheter-based device for drug delivery according to its expanded position of the present invention.

As shown in FIG. 1, the electrodes 24, when relaxed, lie close to the body of the support catheter thereby allowing the catheter to be passed into a blood vessel or other tubular compartment of the body using an introducer. When located in an artery, the electrodes 24 may then be mechanically expanded, as shown in FIG. 2. In the middle region of the expanded electrodes 24, a majority of the individual electrodes 24 are closely juxtaposed to the tissue to be treated. This middle region of the electrodes 24 may be coated with a visco-elastic polymer matrix incorporating the drug or other therapeutic agent to be locally delivered into the tissue. Although the electrode array is radio opaque, positioning of the catheter 10 in the treatment zone may be further assisted by strategically placed radio-opaque markers located on the support catheter body.

In the first embodiment suitable for iontophoresis, the electrodes 24 preferably comprise stainless steel wire. The electrodes are preferably integral to a short length (~2–6 cm) of the braided polyester filament sleeve 20 which fits closely over the support catheter 10 near the distal end 14. In one variation, the electrodes 24 comprise 316 graded stainless steel wire (or similar conductive metal or carbon fiber). The wire for the electrodes 24 is preferably able to be bent without kinking. Preferably, the electrodes 24 should have a thickness of from about 0.10 to about 0.20 mm. More preferably, the electrodes 24 should have a thickness of from about 0.12 to about 0.14 mm. The thickness is determined by the outside diameter of the support catheter 10 and the number and spacing of the electrodes 24 around the support catheter 10 which are required for a particular treatment strategy. The electrode wires can be intercalated between polyester monofilaments 28 having approximately the same diameter as the electrodes 24. The polyester monofilaments 28 provide structural support to the network during spinning of the braided sleeve 20 and also when the braided sleeve 20 is expanded. The polyester monofilaments 28 also assist in allowing the network to be compressed such that it fits closely to the catheter body for ease in passing the device down an introducer, along a vessel or in withdrawal of the catheter into the sleeve and out of the body after use.

The electrodes 24 and the polyester monofilament fiber 28 are preferably formed by spinning. During the spinning of the braid, the electrode wire 24 and polyester fiber 28 are fed into the machine from different spools and become configured into a parallel array around the circumference of the tubular sleeve 20. The sleeve 20 is spun to an internal diameter that fits closely over the support catheter 10 and is then cut to a length determined by the degree of expansion of the sleeve required for a particular delivery application. In practice, a length of 3–5 cm and a maximum sleeve expansion of from about 120 to about 150 percent, with respect to the initial resting diameter, will be suitable for most tissue applications. However, the amount of expansion may vary with the different tissue structures to be treated. The number of spools used during spinning determines the openness of the weave when the sleeve is expanded.

Figure 3:
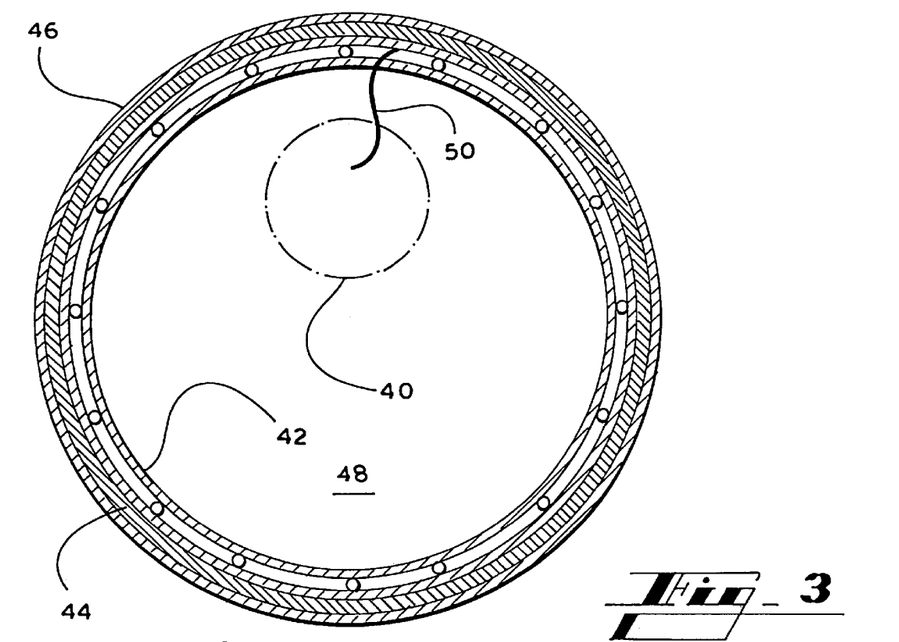
FIG. 3 is a cross-sectional view taken along line a—a of the catheter-based device according to a first embodiment of the present invention.

The electrodes 24 and non-conductive polyester monofilaments 28 are held tightly at each end of the sleeve 20 using ferrule rings 34, 36. The ferrule rings 34, 36 may be made from any material such as metal or plastic. The ferrule 34 at the distal end 14 of the electrode sleeve 20 is usually fly fixed to the support catheter 10. However, the ferrule 36 at the proximal end 12 is able to selectively slide axially back and forth along the support catheter body 10. Movement of this proximal end 12 ferrule 36, with respect to the support catheter 10, controls the degree of expansion of the electrode network. The electrodes 24 are usually bonded to the ferrule ring 34 in the distal end 14 such that good electrical continuity exists. As shown in FIG. 3, The wire lead 50 emerging from the internal lumen 40 of the support catheter 10 near the distal end 14 ferrule 34 is bonded thereto and serves to connect the electrodes 24 in the sleeve to a power supply unit (not shown). The proximal end 12 ferrule 36, which is free to move on the catheter body, is preferably similar in construction to the distal ferrule 14 with the electrode wires 24 and polyester monofilaments 28 bonded within it. However, there is no connection of the electrodes 24 to the power supply within the proximal ferrule 12. The outer coating of both ferrules 34, 36 is preferably made from a non-conductive material. The remainder of the catheter interior 48 is used as a guide wire lumen.

The fixed distal end ferrule 14 may include an inner insulating ring 42 and/or an insulating coat 44. These insulating layers may be of any known insulating material, such as plastics, polyvinyl-polyethylene composites. Examples of materials useful in the present invention include plastics such as TEFLON®. Additionally, a metal ring 46 may be included for attachment to the electrode wires.

In operation, the catheter 10 is placed near the target cells. When the catheter 10 is in position for treatment with the electrode network adjacent to the treatment area, the ferrule ring 36 is manipulated to expand (or balloon out) the electrode sleeve 20 into an open mesh network. The degree of expansion depends on the bore of the artery, but it is controlled so that the electrodes 24 press firmly on the vessel wall tissue. To effect the network expansion, the proximal end of the free sliding ferrule 36 is held stationary using a close fitting outer guide catheter tube 38. The outer catheter tube is sleeved over the support catheter body 10 from the proximal end 12 until it abuts the end of the proximal end 12 ferrule 36. While holding the outer catheter tube (not shown) in position against the ferrule 36, the support catheter 10 is then slowly drawn back towards the proximal end 12 fixed ferrule 36. This movement forces the electrodes 24 to expand outward from the catheter body 10 so that the electrodes 24 can press fly against the tissue area to be treated, such as the luminal face of an artery. This reciprocal manipulation of the catheter 10 and guide sleeve can be pre-calibrated for different degrees of network expansion appropriate to the vessel bore in the area to be treated. If needed, the expansion/relaxation sequence may be mechanized using a motorized ratchet device which controls the movement of the support catheter 10

One of the novel and important features of the present invention is that since the polymer coating is present only in the middle region of the electrodes 24, after expansion of the network, the polymer matrix is positioned on the vessel wall or tissue. There are adequate open interstices in the remainder of the network closer to the support catheter body 10 for blood to flow through the artery during electrical pulsing and drug delivery. This is greatly advantageous over catheters having electrodes positioned within or on the surface of an occlusive balloon in terms of reducing ischaemic risk. Although a perfusion lumen is generally incorporated in the catheter body of iontophoretic balloon catheters, these perfusion lumens bypass the occluded region and only prevent ischaemia downstream of the occluding balloon. Such catheters rarely provide an adequate blood flow rate for drug delivery treatment schedules extending beyond about one minute. The design of the present invention obviates the need for a perfusion lumen.

In using the present device for iontophoretically enhanced drug delivery, a separate plate electrode of opposite polarity to the catheter electrodes is used in order to generate the potential gradient across the artery or other body tissue. This plate electrode is positioned elsewhere on the patient's body (usually the skin) and may be attached using any known means, such as ECG conductive jelly.

The polarity direction for the network and plate electrodes is selected according to the charge characteristics of the treatment agent to be delivered. Positively charged agents will iontophoretically migrate towards the negatively charged electrode and vice versa.

A second embodiment of the present invention uses a printed circuit board for the electrodes 24. This embodiment allows for drug delivery using only iontophoretic enhancement, drug delivery using only electroporation, or a combined strategy involving the initial delivery of the drug into the artery wall using pre-iontophoresis, followed by electroporation of the tissue cells to facilitate cellular entry of the drug for targeting intracellular structures or pathways.

In this second embodiment, the catheter body 10 is essentially the same as shown in FIG. 1. However, the electrode array 24 is of a different construction and consists of a series of very narrow tapes 70 formed by making a series of parallel slots 90 cut in the middle region of a rectangular flexible printed circuit board. The board can be rolled into a cylinder and affixed to the catheter body 10 within the two ferrules. The distal ferrule 14 is fixed to the catheter body 10 and the proximal ferrule 12 is free to move axially. The slots 90 do not extend the full length of the rectangle. An uncut connected region 92 is left at each end for fitting into ferrules. The electrode array 24 is constructed by etching out a flat metal sheet, such as copper, gold platinum, silver or titanium, which is attached to a base material. Preferably, printed circuit board comprises a polyimide/copper sandwich. The base and metal sheet sandwich is rectangular with the short sides being of a length equal to the circumference of the catheter 10 such that when the sheet is rolled into a cylinder to fit into the ferrules 34 on the support catheter 10, there will be no overlap. The length of the longer side of the rectangle will be determined by the amount of electrode expansion required for a particular application. The paired electrode tracks are etched into this plate by a conventional procedure familiar to those skilled in the art of PCB manufacture. Preferably, the entire PCB is coated with a thin layer of gold on its upper copper surface.

Figure 4:
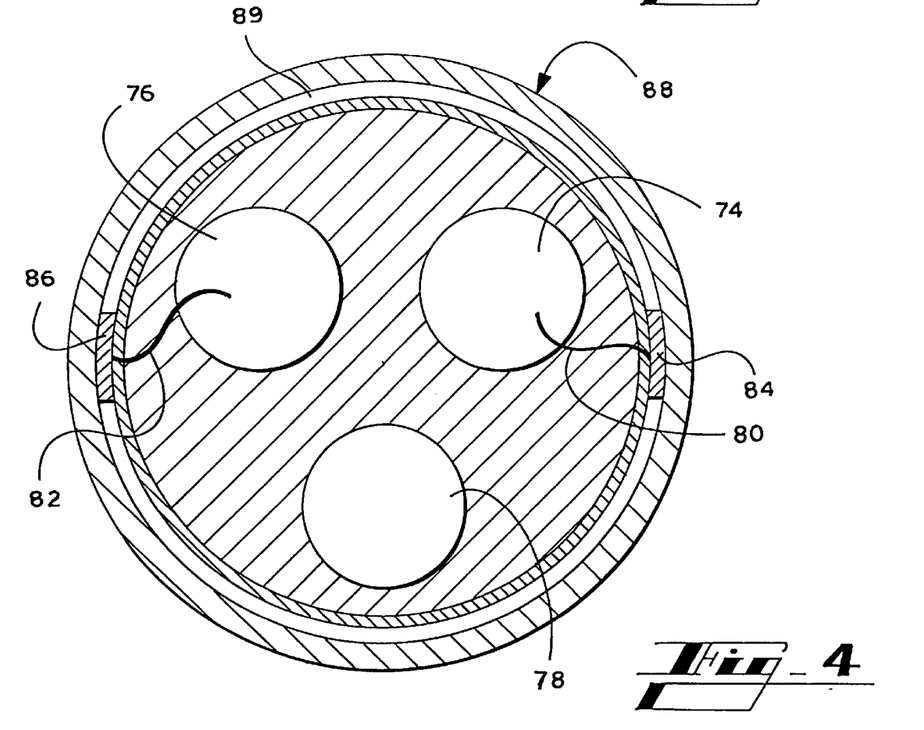
FIG. 4 is a cross-sectional . view taken along line a—a of the catheter-based device according to a second embodiment of the present invention.

As shown in FIG. 4, the cross-sectional area of the catheter includes an internal lumen 74 for the positive lead, an internal lumen 76 for the negative lead, a lumen for the guide wire 78 and lead wires 80, 82 for the respective positive and negative leads. Positive and negative collecting plates 84 and 86 are bonded directly to the appropriate polarity wire emerging from the catheter lumen. Finally, as discussed above, insulating layers 88, 89 may be included.

In a preferred design arrangement, the collecting plates are oriented such that, when the PCB plate is rolled into a cylinder, the collecting plates are located at opposite sides of the catheter.

The commercial procedure for making such conductive tracks in the copper is familiar technology to those skilled in the art of integrated circuitry manufacture, minicomputer motherboard production and other forms of micro circuitry instrumentation. The electrodes may be coated with a thin layer of gold after production if desired. This coating is able to prevent oxidation processes occurring on the electrodes which would affect their efficiency.

In one of these procedures, a series of slots 90 are made right through the PCB giving a row of separate tapes. Each series of slots 90 carries a pair of electrodes 24 of opposite polarities. These slots 90 allow the electrode array to expand outwards to press against the vessel wall when the ferrules 34 on the catheter body 10 are brought closer together, as described above. The slots 90 preferably do not extend the length of the PCB plate, but instead a narrow strip 92 is left unslotted at each end joining the individual tapes together. In the joined region at one end of the PCB, tracks are etched to connect one of each pair of electrodes to a collecting plate in the corner of the PCB. The remaining electrodes 24 of each pair are similarly tracked to a common collecting plate situated halfway along the end region. This separation of the two collecting plates by a distance roughly equal to half the eventual tubular circumference creates good insulation and also allows the lumen lead wires to emerge from the catheter body on opposite sides. Each tape carries a pair of electrodes 24 of opposite polarities with a narrow electrode gap space between them.

Figure 5A:
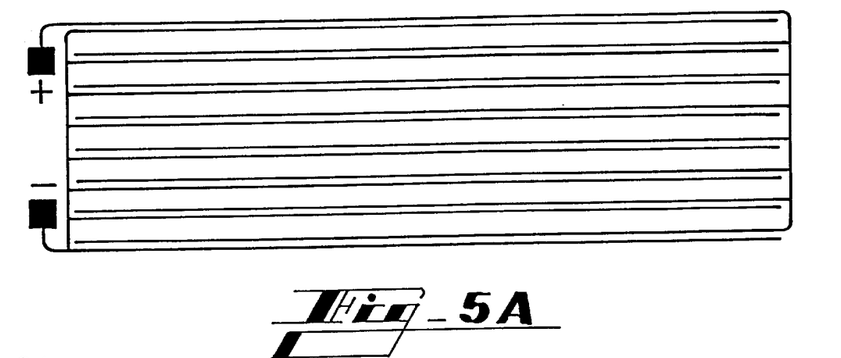
FIG. 5(a) shows the electrode network of a PCB electrode according to a second embodiment of the present invention.
Figure 5B:
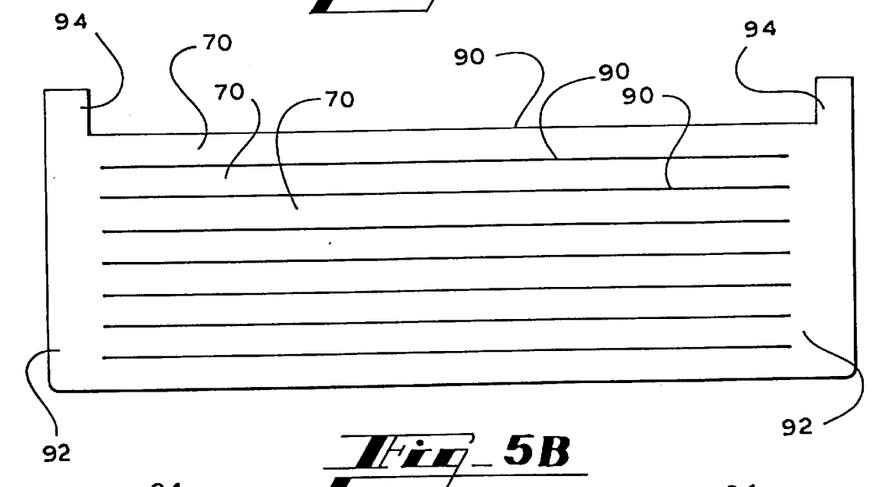
FIG. 5(b) shows the base layers and the location of etched slots in a PCB electrode according to a second embodiment of the present invention.
Figure 5C:
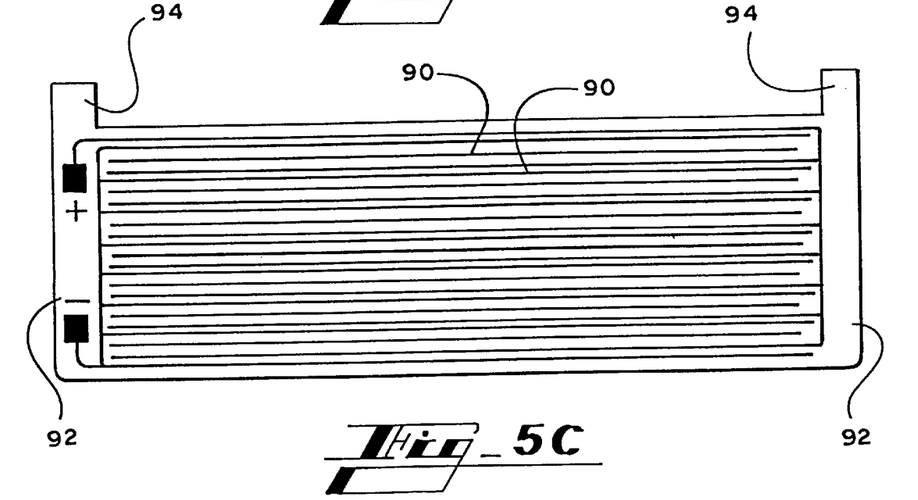
FIG. 5(c) shows a composite detailed diagram of the base with slots and the electrode network of a PCB electrode according to a second embodiment of the present invention.

FIG. 5(a) shows the PCB with the paired electrode tracks and the collecting plates connected to electrodes 24 of the same polarity. FIG. 5(b) shows the PCB with only the slots 90 drawn. FIG. 5(c) shows all the features in detail including the slots 90 and the paired electrode tracks.

In a preferred embodiment, there are 8 parallel pairs of electrodes 24, with each electrode being from about 0.15 to about 0.3 mm wide. More preferably, the electrodes are about 0.2 mm in width with a gap width of 0.2 mm. Preferably, the electrodes 24 extend the full depth of the metal sheet 70, preferably of copper, down to the base material 72, preferably a polyimide. The electrode gaps between each pair would be about the width of the electrodes, also about 0.2 mm. However, the distance between the electrodes 24 and the slots 90 and the distance between the electrodes 24 and the edge of the PCB plate is preferably about 0.5 mm. Smaller distances (from about 0.125 to about 0.2 mm) are possible for PCB cylinders suitable for mounting on catheters of outer dimensions as low as 2 mm.

Depending on the size and thickness of the PCB electrode strips, an additional support layer may be needed in order to ensure that, when used, the electrodes 24 expand outward and contact the vessel walls. This additional support may be accomplished by providing an additional layer of polyimide specifically to the middle region on the underside of the PCB strips. Alternatively, when forming the electrode tracks, it may be possible to control the etching process to selectively etch certain portions of the PCB plate such that the electrodes on the strips have greater structural strength in the bonded regions.

At each end of the PCB plate, the joining strip is extended on one side to give a tab 94 which facilitates the fixing of the tubular formed electrode 24 array into the ferrules 34, 36 on the catheter body 10. These ferrules are preferably short plastic (non-conductive) cylinders into which each end of the tubular electrode 24 array is bonded. In the fixed ferrule at the distal end 14, an electrical connection is made between the electrode collecting plates and the appropriate lumen leads (not shown) emerging from the catheter 10 under the fixed ferrule. By tracking the electrodes 24 of different polarities to separate collecting plates at the fixed ferrule end of the electrode 24 array, no lumen lead connection is required in the free moving ferrule 36 at the proximal end 12 of the electrode array. This ferrule is bonded only to the joining strip of the PCB and not to the catheter body.

Figure 6:
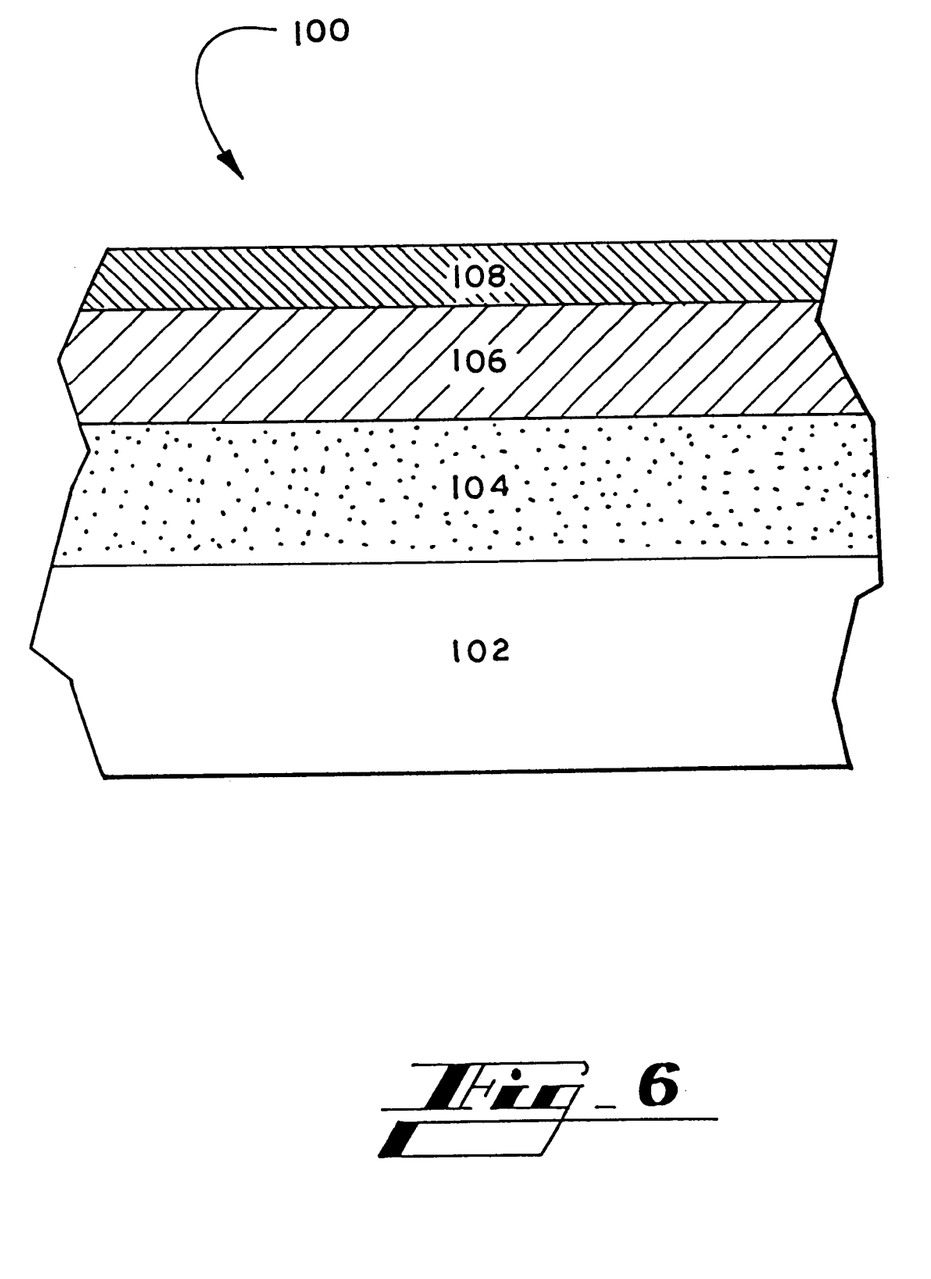
FIG. 6 shows a cross-sectional view of a preferred PCB electrode embodiment.

In FIG. 6, the preferred embodiment of the PCB electrode 100 is provided. This embodiment includes a flexible polyimide base layer 102, a copper electrode layer 106 and a glue or other adhesive layer 104 for binding the polyimide layer 102 to the copper electrode layer 106. Additionally, the PCB electrode 100 includes a gold coating 108 on the copper electrode layer 106. Preferably, the polyimide base layer 102 is about 50 microns in thickness, the glue or adhesive layer 104 is about 25 microns in thickness, the copper electrode layer 106 is about 17.5 microns in thickness and the gold coating 108 is about 2 microns in thickness. Also, in the preferred embodiment, the PCB plate carrying 8 pairs of electrodes has a short side dimension of 0.592 inches (15.037 mm). Rolled into cylindrical form along ifs long side results in a tubular electrode array that fits closely to a catheter body having an outer diameter of 3.9 mm. However, while these are the preferred dimensions, PCB plates are commonly made that are sufficiently flexible such that they may be rolled into a cylinder having a radius as small as 10 times their thickness. One skilled in the art will recognize that by reducing the thickness of the polyimide/copper PCB plate, by reducing the electrode spacing and slot edge to electrode track spaces, and/or by varying the number of paired electrode tracks, it would be possible to fabricate a PBC electrode array that is capable of fitting onto a 2–3 mm outer diameter catheter body, or even smaller.

The length of the catheter along the long side may be selected as needed. However, in a preferred embodiment, the catheter has a length of 1.571 inches (39.903 mm). However, the catheter length may be varied to allow for different expansion diameters also to allow for short or long segments of the target tissue to be treated. In one variation of this embodiment, the distal end fixed ferrule may include metal plates or studs in the ferrule which are connected to the appropriate lumen leads. The electrode would be a preformed cylindrical cassette-type electrode with an integral proximal end ferrule. Each cassette electrode would have the same diameter to fit a particular catheter body and also having at one end connectors which connect with the metal plates or studs in the fixed ferrule. Then, depending on the treatment parameters required, different cassette electrodes could then be used by sliding them onto the catheter and "plugging in" the proper cassette electrode into the distal end fixed ferrule. These cassettes could be preloaded with polymers containing different drugs.

When used for electroporation, the catheter may be connected to a suitable pulse generator. The generator sends pulses to the tissue across narrow electrode gaps. These pulses are preferably of a field strength (volts/cm.) in the range used for cell electroporation and generated at low and physiologically acceptable peak input voltages. For example a peak input voltage of, for example, 30 volts with electrode gap widths of 0.2 mm would give a field strength of 1.5 kV/cm. (i.e. 50×30 volts). A reduction in electrode gap width or an increase in input voltage would give a corresponding increase in field strength.

Additionally, the lumen leads may be modified such that power is only delivered to a few of the electrodes. In this manner, only the portion of the vessel walls that requires treatment would be treated. This may be accomplished by taking the leads for selected electrode pairs right through the catheter lumens to the power supply where they can be switched "on" or "off" according to need. Polarity selection in the ferrule could be achieved by an electrode of one polarity passing through the polyimide base material through "vias" or holes to a common terminal on the underside of the PCB. This is a common configuration in printed circuit boards. In this way, treatment can be restricted to a segment of the luminal circumference.

The electrodes in the device may also be all switched to single polarity for use with an external plate electrode for iontophoresis or switched to electrode pairs of opposite polarity for electroporation. In the latter procedure, an external plate electrode is not required and this is simply disconnected at the power supply.

Iontophoretically enhanced delivery requires that the therapeutic agent carry a net charge under physiological conditions whereas electroporation alone would be used for delivering treatment agents that are not sufficiently ionized to iontophorese well into tissues. Electroporation may also be the preferred strategy for enhancing localized cellular targeting of a systemically administered agent such as in tumor chemotherapy. Anti-tumor, anti-mitotic or anti-neoplastic agents include, but are not limited to, alkaloids, anthracyclines, platinum conjugates, antimetabolites, DNA alkylating agents, antisense oligonucleotides, folic acid and purine antagonists, immunomodulators, interleukins antibody conjugates, anti-growth factors, and anti-angiogenic factors and the corresponding receptor antagonists, as also various phosphodiesterase and protein kinase inhibitors.

The combined use of pre-iontophoresis followed by electroporation may be appropriate for local delivery of drugs that penetrate intact cell membranes poorly or not at all or where a high extracellular concentration is required for rapid diffusion through the transient electropores to an intracellular target.

The catheter may be used, as discussed above, in a combined iontophoresis/electroporation process, such as for an angioplasty procedure. First, after balloon dilatation, a period of continuous or pulsed iontophoresis would first be applied to enhance drug migration out of the polymer coating and into the artery wall tissue to raise the drug concentration to a sufficiently high level within the tissue extracellular spaces. Since blood is still able to flow through the artery during electrical pulsing, iontophoretic delivery can be extended for much longer periods than is possible with delivery devices using fully occlusive balloons. After iontophoretic delivery, and without removing or repositioning the catheter, the electrodes on the catheter would be switched from their single polarity to the paired electrode mode in each PCB strip. The vessel wall would then be subjected to a series of high field strength, very short time electroporation pulses to transiently electroporate the surface membranes of cells in the artery wall tissue. The drug in the extracellular spaces of the tissue is then able to rapidly diffuse down a concentration gradient through the open cell membrane pores, enter the cell's cytosol compartments for targeting to intracellular structures such as the nucleus, cytoskeletal elements and metabolic or signal transduction pathways. The porated cell membranes would subsequently reseal with full restoration of cell integrity.

Finally for withdrawal of the device after treatment, the guide (sleeve) catheter used for electrode network expansion would be returned to its original placement and the catheter would be removed.

The treatment agent may be delivered through the catheter using several different embodiments. In one embodiment, which may be used with any of the catheter embodiments set forth, the treatment agent is incorporated within a polymer matrix, and this matrix is applied as a coating to the middle region of the electrode array. The treatment agent is may then be iontophoretically driven out of this polymer matrix into the adjacent tissue. The polymer matrix preferably has a good drug holding capacity and is sufficiently pliant to be compressed against the tissue when the electrode network is expanded.

In a second embodiment, the polymer matrix containing the drug is instead molded into a short tubular expandable visco-elastic sleeve which fits over the middle region of the electrode array in its relaxed position. When the electrode network is expanded, the polymer sleeve expands as well until it is pressed against the tissue to be treated. In a third embodiment, the drug holding polymer matrix may be prelaid or prepolymerized as a "lawn" or "paving" on the surface of the tissue to which the electrodes are subsequently juxtaposed for iontophoretically moving the treatment agent out of the polymer and into the adjacent tissue.

With respect to the polymer composition, the term "polymer matrix" as used herein includes synthetic hydrogel polymers with pores or interstices of different sizes and capacities introduced during manufacture, and a variety of synthetic elastomers and naturally occurring polymeric materials known to those skilled in the art. The drug or therapeutic agent can be incorporated in the matrix either during polymer production or added after coating or molding of the polymer into the desired shape. Additionally, many of a number of different polymeric materials and methods of fabrication may be used to form the polymer matrices used in the present invention. Examples of suitable polymer materials or combinations include, but are not limited to, biocompatible and/or biodegradable polymers such as poly(lactides), polyglycolides, polyanhydrides, polyorthoesters, polyactals, polydihydropyrans, polycyanoacrylates and copolymers of these and polyethylene glycol. These can take the form of co-polymer hydrogels or cross-linked polymer networks into which drugs for electrically enhanced local delivery can be incorporated either during polymerization or, in the case of certain hydrogels, loaded subsequently. Preferable matrices would be tailored according to the molecular characteristics of the agent to restrict it's loss by free diffusion outwards but allow full iontophoretic migration outwards when a potential is applied across the polymer and adjacent tissue.

In another embodiment, hollow microspheres may be used to deliver the drug or treatment agent. The drug is located within the hollow portion of the microsphere. The drug-laden microspheres may then be injected near the tissue to be treated and activated by the catheter thereby driving the drug from the microspheres into the tissue. A plurality of different drugs may be delivered by using multiple types of microspheres and varying frequencies to deliver the different drugs as needed. Microspheres useful in the present invention include those sold under the name biSphere™ available from POINT Biomedical (San Carlos, Calif.). These microspheres are 3–6 $\mu$m in diameter, feature double-walled construction and are fully biodegradable.

Additionally, normal drug delivery means may be used as well, such as free fluid form. However, use of polymer matrices has certain advantages over free fluid delivery. Delivery of an agent which has been incorporated into a polymer matrix doe not require additional lumens in the support catheter to convey the free fluid drug solution into and out of the treatment site. Additionally, the polymer matrices eliminate the risk of downstream leakage of drug solution due to defective balloon sealing of vessel segments, thereby avoiding the risk of exposure of non-target tissue to high concentrations of the drug. Also, since extra liquid drug delivery lumens are not required, the catheter profile is narrower which improves its maneuverability in the body and reduces production costs.

Additionally, the catheter-based devices of the present invention may be used in other types of treatment processes, such as ultraviolet photolysis or photodynamic therapy and sonophoresis (or phonophoresis). For use with these processes, the PCB electrode array may have incorporated fiber optic filaments or, for sonophoresis, piezoelectric transducers which would provide the requisite treatment means to carry out the respective treatment process. In the case of fiber optics, some of the stainless steel electrodes in the first embodiment electrode array would be replaced with fiber optic filaments whose optical continuity would be continued through the ferrule and down the lumen of the catheter to the light source outside the body.

We claim:

1. A catheter-based device for enhancing the local delivery of a treatment agent into target tissues of a body vesicle or organ comprising:
   a catheter having a proximal end, a distal end and a middle region; and
   an electrode network at the distal end of the catheter comprising a plurality of electrodes and having a proximal end, a distal end and a middle region; wherein the electrode network is constructed and arranged such that when the electrode network is in a relaxed position, the electrodes lie substantially flat and when the electrode network is in an expanded position, the electrodes are closely juxtaposed to the target tissues without occluding fluid flow through the body vesicle; and
   a polymer matrix incorporating the treatment agent is located around at least the middle region of the electrode network of the catheter.

2. The catheter-based device of claim 1, wherein the electrodes comprise metal wire.

3. The catheter-based device of claim 2, wherein the electrodes comprise stainless steel.

4. The catheter-based device of claim 2, wherein the electrode network further comprises polyester monofilaments intercalated between the metal wire electrodes.

5. The catheter-based device of claim 2, wherein the electrodes have a thickness of from about 0.10 to about 0.20 mm.

6. The catheter-based device of claim 1, wherein the electrodes comprise a plurality of printed circuit board electrode strips.

7. The catheter-based device of claim 6, wherein the printed circuit board electrode strips comprise a conductive metal layer attached to a base material.

8. The catheter-based device of claim 7, wherein the metal layer is copper.

9. The catheter-based device of claim 7, wherein the base material is polyimide.

10. The catheter-based device of claim 6, wherein the printed circuit board electrode strips are formed by a process comprising:
   attaching a flat metal sheet to a base material sheet to form a rectangular sheet having one side longer than the other;
   etching electrode tracks and cutting parallel slots in the rectangular sheet to form the plurality of printed circuit board strips; and rolling the rectangular sheet such that the rolled sheet is able to comprise the electrode network.

11. The catheter-based device of claim 6, wherein the printed circuit board electrode strips are from about 0.15 to about 0.3 mm in width.

12. The catheter-based device of claim 1, further comprising a ferrule located at the distal end of the electrode network and a ferrule located at the proximal end of the electrode network.

13. The catheter-based device of claim 12, wherein the distal end ferrule and the proximal end ferrule are constructed and arranged such that the distal end ferrule is fixed on the catheter while the proximal end ferrule is capable of sliding axially to and fro along the catheter thereby causing the electrode network to be either in the relaxed position or the expanded position.

14. A method of delivering a treatment agent into target tissues of a body vesicle comprising:

applying a treatment agent encompassed within the polymer matrix to at least a portion of the electrode network of the catheter-based device of claim 1;

expanding the electrode network such that the electrodes closely juxtapose the target tissues without occluding fluid flow through the body vesicle; and applying means for driving the treatment agent from the electrode network into the tissue walls.

15. The method of claim 14, wherein the means for driving the treatment agent from the electrode network into the target tissues comprise iontophoretic means.

16. The method of claim 15, further comprising electroporation means to further drive the treatment agent from the electrode network into the target tissues.

17. The method of claim 14, wherein the means for driving the treatment agent from the electrode network into the target tissues comprise electroporation means.

18. The method of claim 14, wherein the treatment agent is applied to at least a portion of the electrode network by admixing the treatment agent within the polymer matrix and coating the admixture onto the surface of the electrodes.

19. The method of claim 14, wherein the treatment agent is applied to at least a portion of the electrode network by forming a visco-elastic sleeve comprising the treatment agent and the polymer material and placing the visco-elastic sleeve around the middle region of the catheter such that when the electrode network is expanded, the electrodes expand the visco-elastic sleeve outward such that an outer surface of the visco-elastic sleeve closely juxtaposes the target tissues of the bodily vesicle.

20. The method of claim 14 wherein the treatment agent is included in the polymer matrix paving applied to, or polymerized in situ on, the target tissues and the expanded electrode network is subsequently juxtaposed and energized to drive the agent out of the polymer matrix and into the target tissue.

* * * * *